United States Patent
Lewis et al.

(10) Patent No.: US 10,755,700 B2
(45) Date of Patent: Aug. 25, 2020

(54) SYSTEMS AND METHODS FOR OPERATING A VOICE-BASED ARTIFICIAL INTELLIGENCE CONTROLLER

(71) Applicant: Ascension Health Alliance, St. Louis, MO (US)

(72) Inventors: Gerry X. Lewis, St. Louis, MO (US); Juan Sanchez, Annapolis, MD (US); Christine K. McCoy, St. Louis, MO (US); John Pirolo, Franklin, TN (US); Fahad Tahir, Nashville, TN (US)

(73) Assignee: Ascension Health Alliance, St. Louis, MO (US)

( * ) Notice: Subject to any disclaimer, the term of this patent is extended or adjusted under 35 U.S.C. 154(b) by 153 days.

(21) Appl. No.: 16/015,540

(22) Filed: Jun. 22, 2018

(65) Prior Publication Data

US 2018/0374475 A1    Dec. 27, 2018

Related U.S. Application Data

(60) Provisional application No. 62/524,263, filed on Jun. 23, 2017.

(51) Int. Cl.
*G10L 15/18*    (2013.01)
*G06N 3/08*    (2006.01)
(Continued)

(52) U.S. Cl.
CPC .......... *G10L 15/1815* (2013.01); *G06N 3/006* (2013.01); *G06N 3/0454* (2013.01);
(Continued)

(58) Field of Classification Search
CPC .................................................. G10L 15/1815
(Continued)

(56) References Cited

U.S. PATENT DOCUMENTS 6,081,782 A    6/2000    Rabin
6,829,603 B1 *    12/2004    Chai ................... G06F 16/3344
(Continued)

FOREIGN PATENT DOCUMENTS

WO    2015196115 A1    12/2015

OTHER PUBLICATIONS

International Search Report for related Application No. PCT/US2018/038962, dated Jun. 22, 2018, 13 pages.

*Primary Examiner* — Susan I McFadden
(74) *Attorney, Agent, or Firm* — Armstrong Teasdale LLP

(57) ABSTRACT

A system for voice-based process management is provided. The system includes a microphone, a speaker, and a computer device in communication with the microphone and the speaker. The computer device includes at least one processor in communication with at least one memory device. The computer device is programmed to (i) receive, via the microphone, one or more audible statements from an individual; (ii) parse the one or more audible statements into discrete data elements to allow normalized semantic definition of the meaning of conveyed information; (iii) compare the conveyed information with stored data; (iv) determine whether there is a discrepancy based on the comparison; and (v) if the determination is that there is a discrepancy, request, via the speaker, a clarification.

20 Claims, 6 Drawing Sheets

(51) Int. Cl.

| | |
|---|---|
| *G10L 17/00* | (2013.01) |
| *G10L 15/22* | (2006.01) |
| *G16H 40/67* | (2018.01) |
| *G16H 40/20* | (2018.01) |
| *G16H 80/00* | (2018.01) |
| *G06N 3/04* | (2006.01) |
| *G06N 3/00* | (2006.01) |
| *G06N 5/04* | (2006.01) |
| *G06N 20/10* | (2019.01) |
| *G16H 50/70* | (2018.01) |
| *G10L 15/16* | (2006.01) |
| *G06F 3/16* | (2006.01) |
| *G06N 7/00* | (2006.01) |
| *G06N 5/00* | (2006.01) |
| *G10L 15/26* | (2006.01) |
| *G06N 5/02* | (2006.01) |

(52) U.S. Cl.
CPC ............... *G06N 3/08* (2013.01); *G06N 3/088* (2013.01); *G06N 5/041* (2013.01); *G06N 20/10* (2019.01); *G10L 15/1822* (2013.01); *G10L 15/22* (2013.01); *G10L 17/005* (2013.01); *G16H 40/20* (2018.01); *G16H 40/67* (2018.01); *G16H 50/70* (2018.01); *G16H 80/00* (2018.01); *G06F 3/167* (2013.01); *G06N 3/04* (2013.01); *G06N 5/003* (2013.01); *G06N 5/025* (2013.01); *G06N 7/005* (2013.01); *G10L 15/16* (2013.01); *G10L 15/26* (2013.01); *G10L 2015/223* (2013.01)

(58) Field of Classification Search
USPC .......................................................... 704/246
See application file for complete search history.

(56) References Cited

U.S. PATENT DOCUMENTS

| | | | |
|---|---|---|---|
| 7,489,766 | B2 | 2/2009 | Morganstein et al. |
| 9,098,467 | B1 | 8/2015 | Blanksteen et al. |
| 9,108,450 | B2 * | 8/2015 | Buser .................... B33Y 40/00 |
| 9,483,459 | B1 * | 11/2016 | Riley ..................... G10L 25/48 |
| 2006/0184364 | A1 | 8/2006 | Benja Athon et al. |
| 2006/0184367 | A1 | 8/2006 | Benja Athon et al. |
| 2006/0184388 | A1 | 8/2006 | Benja Athon |
| 2006/0200366 | A1 | 9/2006 | Benja Athon |
| 2006/0241943 | A1 | 10/2006 | Benja Athon et al. |
| 2006/0287849 | A1 | 12/2006 | Benja Athon et al. |
| 2006/0288225 | A1 | 12/2006 | Jung et al. |
| 2007/0043554 | A1 | 2/2007 | Benja Athon et al. |
| 2008/0059182 | A1 | 3/2008 | Benja-Athon et al. |
| 2009/0150156 | A1 | 6/2009 | Kennewick et al. |
| 2009/0299924 | A1 | 12/2009 | Bauer et al. |
| 2011/0231353 | A1 | 9/2011 | Wang et al. |
| 2012/0101841 | A1 | 4/2012 | Kobayashi |
| 2013/0006626 | A1 | 1/2013 | Aiyer et al. |
| 2013/0218572 | A1 | 8/2013 | Cho et al. |
| 2014/0316764 | A1 | 10/2014 | Ayan et al. |
| 2015/0164436 | A1 | 6/2015 | Maron et al. |
| 2015/0238692 | A1 | 8/2015 | Peterson et al. |
| 2015/0332196 | A1 | 11/2015 | Stiller et al. |
| 2015/0339356 | A1 | 11/2015 | Myslinski |
| 2017/0318013 | A1 | 11/2017 | Roy et al. |

* cited by examiner

SYSTEMS AND METHODS FOR OPERATING A VOICE-BASED ARTIFICIAL INTELLIGENCE CONTROLLER

CROSS REFERENCE TO RELATED APPLICATIONS

This application claims the benefit of U.S. Patent Provisional Application No. 62/524,263, entitled "SYSTEMS AND METHODS FOR OPERATING A VOICE-BASED ARTIFICIAL INTELLIGENCE CONTROLLER," which was filed Jun. 23, 2017, which is hereby incorporated by reference in its entirety.

BACKGROUND

The present disclosure relates to operating a voice-based, artificial intelligence controller and, more particularly, to network-based systems and methods for authenticating and verifying information received via voice-based communications from one or more users.

In many fields, ineffective team communication is the root cause of a majority of errors. One person in a team may assume that something is correct without confirming with others. When performing a procedure with a series of process steps, these types of incorrect assumptions can lead to significant errors. In some cases, some errors may be prevented through adherence to standardized process protocols and guidelines. However, failing to properly adhere to those standardized protocols and guidelines may not prevent those errors from occurring. Wrong-site surgical errors are exemplary of this type of process error. For a variety of reasons, a surgeon may assume that the patient's left knee is to be replaced, when it is actually the right knee. Although pre-procedure protocols for site verification exist in orthopedic surgery, if those standardized process steps are not explicitly followed, or are followed but not dynamically confirmed by the operating team, the risk of a wrong-site surgery is increased.

In some cases, electronic record platforms have been used to implement these standardized protocols and guidelines. For a variety of reasons, however, these implementations have not been optimized. These reasons include inefficient workflows within electronic record platforms, failure to provide key information at the appropriate time within the execution of protocols or guidelines, inability to dynamically access information critical to accurate protocol or guideline completion, and poor user interface design. Additionally, the prevalence of incomplete, inaccurate, and potentially uninterpretable data within electronic records complicates the effective real-time execution of protocols and guidelines.

BRIEF SUMMARY

The present embodiments may relate to systems and methods for operating a voice-based artificial intelligence controller. The platform may include a process management (PM) computer system, one or more speakers, one or more microphones, a plurality of user computer devices, and/or one or more databases. The PM computer system may be a server device associated with plurality of locations where processes are occurring or associated with a single location.

In one aspect, a system for operating a voice-based artificial intelligence controller is provided. The system includes a microphone, a speaker, and a computer device in communication with the microphone and the speaker. The computer device includes at least one processor in communication with at least one memory device. The computer device is programmed to receive one or more audible statements from an individual via the microphone. The computer device is also programmed to parse the one or more audible statements into discrete data elements to allow normalized semantic definition of the meaning of conveyed information. The computer device is further programmed to compare the conveyed information with stored data. Moreover, the computer device is programmed to determine whether there discrepancies based on the comparison. If the determination is that there are discrepancies, the computer device is programmed to request a clarification via the speaker.

In another aspect, a computer system for operating a voice-based artificial intelligence controller is provided. The computer system includes at least one processor in communication with at least one memory device. The at least one processor is programmed to receive one or more audible statements from an individual via a microphone. The computer device is also programmed to parse the one or more audible statements into discrete data elements to allow normalized semantic definition of the meaning of conveyed information. The at least one processor is further programmed to compare the conveyed information with stored data. In addition, the at least one processor is programmed to determine whether there are discrepancies based on the comparison. If the determination is that there is a discrepancy, he at least one processor is programmed to request a clarification via a speaker. If no discrepancies are determined, then the information is processed into the appropriate electronic medical record system within a corresponding procedural structured data format.

In yet another aspect, a computer-based method for operating a voice-based artificial intelligence controller is provided. The method is implemented on a computer device including at least one processor in communication with at least one memory device. The method includes receiving one or more audible statements from an individual via a microphone. The computer device is also programmed to parse the one or more audible statements into discrete data elements to allow normalized semantic definition of the meaning of conveyed information. The method further includes comparing the conveyed information with stored data. Moreover, the method includes determining whether there are discrepancies based on the comparison. If the determination is that there are discrepancies, the method includes requesting a clarification via a speaker and receiving the clarification via the microphone.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. It should be understood that each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

Figure 1:
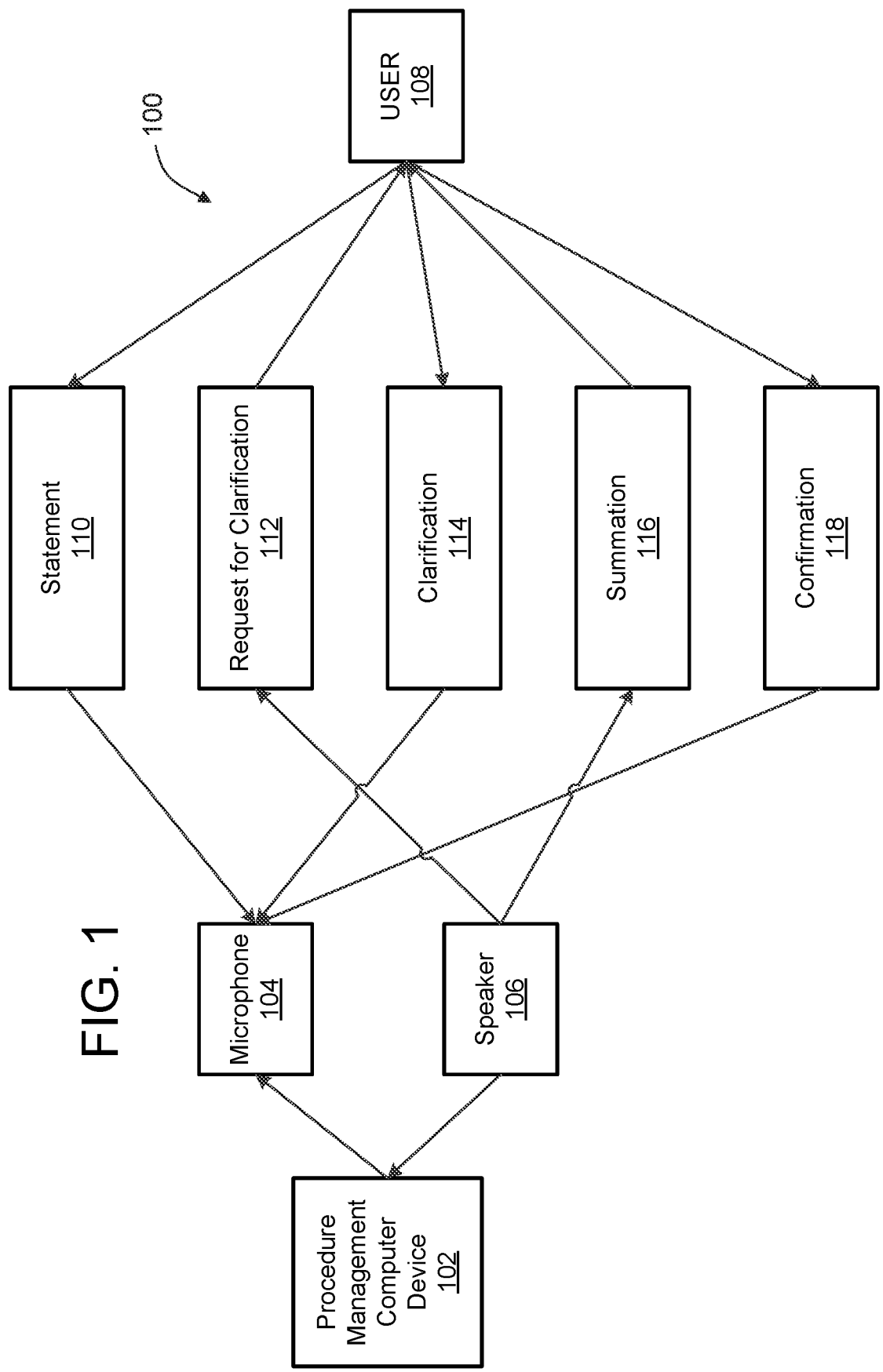
FIG. 1 illustrates a data flow chart of an exemplary process of voice-based procedure management.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION OF THE DRAWINGS

The present embodiments may relate to, inter alia, systems and methods for voice-based procedure management. In one exemplary embodiment, the methods may be performed by a process management ("PM") computer device, also known as process management ("PM") server.

In the exemplary embodiment, the PM server receives one or more audible statements from an individual through a microphone. The one or more audible statements are in a natural language form. The computer device is also programmed to parse the one or more audible statements into discrete data elements to allow normalized semantic definition of the meaning of conveyed information. Conveyed information represents the information that the user desired to transmit to the PM server. For example, a user may state "I am Dr. Smith and am here to perform an appendectomy on Mr. Johnson, patient number #1234." The PM server then parses that statement into the important details: Doctor—"Smith"; Patient—"Mr. Johnson"; Patient Number—"1234"; and operation—appendectomy. The PM server parsing includes abstraction of discrete data into normalized lexical standards.

The PM server compares the conveyed information with already stored data. In the exemplary embodiment, the PM server stores a plurality of data about the procedure or accesses this data from another data store associated with the healthcare provider that is providing the medical procedure to the patient. This information includes data points about the procedure and/or the object of the procedure. In the above example, the PM server compares the important details parsed out of the statement with the stored data. The PM server determines whether there are discrepancies between the conveyed information and the stored data. If the data matches, then the PM server continues with the process sequence. If there is a discrepancy, the PM server requests a clarification through the speaker. In the exemplary embodiment, the request for clarification and/or validation of the information provided is a natural language processing question. The PM server then waits to receive a response from the user. For example, the user may have misstated the patient number as 2153, when it is actually 1235. In this example, the PM server may ask the user to repeat the patient number. Or the PM server may read back the patient number that the user provided and point out the discrepancy and ask for clarification.

In the exemplary embodiment, the PM server stores both the conveyed information and the provided clarifications. In some embodiments, the PM server converts the data into a desired format prior to storing. In some further embodiments, the desired format is in fields in forms. In these embodiments, the PM server populates the fields in those forms based on the conveyed information and the provided clarifications.

In some embodiments, the PM server stores a checklist that includes one or more steps of the procedure. In these embodiments, each step of the checklist includes information that needs to be provided to complete that step. The PM server compares the conveyed information to the checklist and determines the discrepancy based on that comparison. For example, the PM server may determine that one or more steps of the process have not been performed. In these embodiments, the PM server transmits requests for clarification to the user, requesting information necessary to complete the next step.

When the PM server determines that all of the necessary information has been provided, the PM server generates a summation of the conveyed information and the provided clarifications. The PM server plays the summation to the user through the speaker. The PM server waits for the user to confirm the summation and stores both the summation and the confirmation.

A processor or a processing element may employ artificial intelligence and/or be trained using supervised or unsupervised machine learning, and the machine learning program may employ a neural network, which may be a convolutional neural network, a deep learning neural network, or a combined learning module or program that learns in two or more fields or areas of interest. Machine learning may involve improving interpreting natural language audio, determining specific questions to ask for specific procedures, or methods of summarizing information in natural language format.

Additionally or alternatively, the machine learning programs may be trained by inputting sample data sets or certain data into the programs, such as image, mobile devices, accent interpretation, individual identification, and/or procedure step data. The machine learning programs may utilize deep learning algorithms that may be primarily focused on pattern recognition and/or language recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or machine learning.

In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In one embodiment, machine learning techniques may be used to extract data about the computer device, the user of the computer device, the procedure to be performed, the person or item the procedure is to be performed on, geolocation information, image data, audio data, and/or other data.

Based upon these analyses, the processing element may learn how to identify characteristics and patterns that may then be applied to analyzing sensor data, authentication data, image data, mobile device data, and/or other data. For example, the processing element may learn, with the user's permission or affirmative consent, to predict suggestions for offers to present to user and/or offers that processing device may switch to without specifically requesting permission from the user. The processing element may also learn how to verify that the users performing the procedure have the necessary information to properly perform the procedure in question.

At least one of the technical problems addressed by this system may include: (i) improving speed and accuracy of electronic records; (ii) improving regulatory compliance by requiring the proper walkthrough of processes, protocols or guidelines; (iii) validating information provided by participants in the procedures; (iv) providing a convenient platform for performing procedures; and/or (v) preventing typographical errors that may be introduced through human error. The methods and systems described herein describe unconventional and unique systems for analyzing human speech to perform aural checklists based on pre-existing data. These methods and systems describe improvements to existing computer architecture to reduce computer resources by reducing the possibility of errors in a procedure.

The methods and systems described herein may be implemented using computer programming or engineering techniques including computer software, firmware, hardware, or any combination or subset thereof, wherein the technical effects may be achieved by performing at least one of the following steps: (a) receive, via a microphone, one or more audible statements from an individual, where the one or more audible statements are in a natural language form; (b) parse the one or more audible statements to determine conveyed information; (c) compare the conveyed information with stored data; (d) determine whether there is a discrepancy based on the comparison; (e) if the determination is that there is a discrepancy, request, via a speaker, a clarification, where the clarification is a question in a natural language form; (f) receive, via a microphone, the clarification; (g) combine the conveyed information and the clarification into a desired format; (h) store, in the at least one memory device, the conveyed information and the clarification in the desired format; (i) fill out a form based on the conveyed information; (j) generate a summary based on the conveyed information; (k) transmit, via the speaker, the summary to the individual for confirmation; (l) receive, via the microphone, confirmation from the individual; (m) store a checklist including one or more steps of a procedure; (n) compare the conveyed information to the checklist; (o) determine the discrepancy based on the comparison; (p) determine a next step of the one or more steps of the procedure; (q) generate the clarification based on the next step; (r) store one or more data points; (s) compare the conveyed information to the one or more data points; and (t) determine the discrepancy based on the comparison.

In some other embodiments, the technical effects that may be achieved by the system performing at least one of the following steps: (a) receive a plurality of statements from a plurality of individuals, where each individual of the plurality of individuals is associated with a role; (b) parse the plurality of statements into discrete data elements to allow normalized semantic definition of the meaning of conveyed information; (c) identify each individual of the plurality of individuals; and (d) associate the conveyed information associated with that individual with the role associated with the individual.

FIG. 1 illustrates a data flow chart of an exemplary computer-implemented process 100 for voice-based process management. In the exemplary embodiment, a procedure management ("PM") computer device 102 is in communication with a microphone 104 and a speaker 106. The microphone 104 and the speaker 106 are in communication range with a user 108. In some embodiments, PM computer device 102 is in communication with multiple microphones 104 and speakers 106 to provide improved communication with users 108.

In the exemplary embodiment, user 108 makes a statement 110 about a procedure. Statement 110 includes information about the procedure to be performed or that user 108 is currently performing. In the exemplary embodiment, statement 110 is a plain language statement, also known as a natural language. For example, user 108 may state that user is about to replace a patient's left knee. In another example, user 108 may be preparing to perform a forensic investigation of a computer device. Microphone 104 receives statement 110 and transmits statement 110 to PM computer device 102. In the exemplary embodiment, PM computer device 102 parses statement 110 to determine the information conveyed in the statement 110. In the above example, PM computer device 102 parses the statement to determine that the user 108 will be replacing the user's left knee. PM computer device 102 parses the statement 110 into discrete data elements to allow normalized semantic definition of the meaning of conveyed information.

In some embodiments, the first statement 110 includes a code or key phrase that activates PM computer device 102 and instructs PM computer device 102 to start process 100. In these embodiments, PM computer device 102 monitors verbal communication from users 108 through microphone 104, but does not respond or begin process 100 until the key phrase or activation phrases is stated.

In the exemplary embodiment, PM computer device 102 stores data about the procedure. This data is previously stored or accessed by PM computer device 102. This data includes a plurality of data points about the procedure to be performed and about the object or person that the procedure is to be performed on. For example, the information could include patient information about the patient that is about to receive a knee replace or about the computer device that is about to be investigated. This data could have been stored when the patient was initially checked in or registered for the procedure. PM computer device 102 compares the information from statement 110 with the stored data. PM computer device 102 then determines if there is a discrepancy based on the comparison. For example, PM computer device 102 may determine that the stored data states that the procedure is to be performed on the right knee. In another example, the statement 110 may include the patient's name and number, and PM computer device 102 may attempt to confirm that the correct patient is receiving the correct procedure.

If there is a discrepancy, PM computer device 102 generates a request for clarification 112 to ask user 108. In the exemplary embodiment, the request for clarification 112 is a natural language question. PM computer device 102 transmits the request for clarification to speaker 106, which plays the request for clarification 112 to user 108. For example, PM computer device 102 may cause the speaker 106 to ask, "The file says the right knee is to be replaced. Please confirm which knee is to be replaced on Mr. Johnson." The microphone 104 listens for the user 108 to provide a clarification 114 in response to the request for clarification 112. The microphone 104 then transmits the clarification 114 to PM computer device 102. In the above example, user 108 may respond, "Correct, the right knee is to be replaced." In some embodiments, PM computer device 102 may repeat the clarification 114 back to the user 108. For example, "Right knee, agreed." In some further embodiments, PM computer device 102 polls other users 108 to get a consensus on the clarification 114.

Based on the received clarification 114, PM computer device 102 may update the stored data. PM computer device 102 may then analyze the rest of the stored data to determine if there are in additional discrepancies. In the exemplary embodiment, PM computer device 102 stores a checklist of the information necessary to begin or perform the procedure. PM computer device 102 reviews the checklist to determine if all of the steps have been performed. If there are one or more steps left to perform, PM computer device 102 determines the next step to perform and asks the user 108 about that step. For example, the next step may be to confirm that all of the necessary parts or equipment are available to perform the procedure.

In the exemplary embodiment, PM computer device 102 cycles through asking requests for clarification 112 and receiving clarifications 114 until all of the information necessary to begin or perform the procedure has been received. Once all of the required information has been received, PM computer device 102 generates a summation 116 of the information provided by user 108 that PM computer device 102 has confirmed. In the exemplary embodiment, summation 116 is a series of natural language statements. Speaker 106 plays the summation 116 to user 108. PM computer device 102 waits for user's confirmation 118 of the summation 116. In some cases, user 108 may make a correction to the summation 116. In these cases, PM computer device 102 validates user's correction and generates a new summation 116 for the user 108 to confirm. In the exemplary embodiment, once the user 108 provides confirmation 118 of the summation 116, PM computer device 102 completes process 100.

In some embodiments, there may be multiple users 108, such as in an operating room with multiple doctors and/or nurses. In these embodiments, each of the users 108 may provide different statements 110 and/or clarifications 114. In some of these embodiments, PM computer device 102 may associate a role with each of the plurality of users 108. For example, one user 108 may be considered the lead surgeon, a second user 108 may be the assisting physician, and a third user 108 may be a lead nurse. In these embodiments, PM computer device 102 may perform voice recognition analysis and recognize each user 108 by their voice. In some further embodiments, PM computer device 102 may direct requests for clarifications 112 to different users 108 based on their role in the procedure.

In some embodiments, PM computer device 102 applies the received information to one of more forms, where PM computer device 102 populates the fields of the forms with the information received from the user 108.

While the primary example is in an operating room, there are multiple other use cases for process 100. Examples include, but are not limited to, patient intake, determining patient medical history, forensics, manufacturing, construction, demolition, and/or any procedure or process that requires a plurality of steps to be performed and where proper information is important to the proper execution. Other potential applications for process 100 include, but are not limited to, Nursing Admission Assessment, Nursing Shift Assessment, Adverse Event Charting; Medication History documentation, physician/physician assistant (PA)/nurse practitioner (NP)—History & Physician Examination, Procedure Note, Progress Note; Discharge/Discontinue (D/C) Summary, Early Discharge (ED), and "Histories" (e.g. medical, procedural, medication, family).

In some embodiments, there are checklists for prior to the procedure (aka set-up or briefing), just as the procedure is about to begin (aka Time-out prior to beginning), and after the procedure (aka a debriefing). Below are examples of each checklist and then information required to proceed.

The first example checklist would be appropriate as a briefing about the procedure.
1. Patient name: [last, first name]
2. DOB: [mm/dd/yyyy]
3. Procedure: [procedure]
4. Procedure site/laterality: [site/side]
5. Consent(s) signed and available: Yes
6. Site marked by qualified individual: Yes or N/A
7. Patient allergies: No or [allergens]
8. Pulse oximeter on patient: Yes
9. Difficult airway or aspiration risk: Yes
10. STOPBANG Score: [score]
11. Risk of blood loss (>500 mL): No or Yes
12. Blood product status: N/A or [type and screen] or [# of units available]
13. Blood bank product(s) type: [pbc] [platelets] [ffp]
14. Anesthesia safety check completed: Yes
15. All members of the team have discussed care plan and addressed concerns: Yes The second example checklist would be appropriate as a final check just before the procedure is to begin.
1. Introduction of team members: [name:role] [name:role] [name:role] [name:role]
2. Patient name: [last, first name]
3. DOB: [mm/dd/yyyy]
4. Procedure: [procedure]
5. Procedure site/laterality: [site/side]
6. Consent(s) signed and available: Yes
7. Site is marked and visible: Yes or N/A
8. Fire Risk Assessment and prevention methods implemented: Done
9. Relevant images properly labeled and displayed: Yes or N/A
10. Equipment, implants available: Yes or N/A
11. Anticipated Critical Events: [event]
12. Critical or non-routine steps: [steps]
13. Case duration
14. Anticipated blood loss
15. Antibiotic prophylaxis within 1 hour before incision: Yes or NA [antibiotic]
16. Additional concerns: [concerns]
17. Sterilization indicators confirmed: Yes
18. Verification process (all elements above are verified)
19. Document completion of time out: Yes The third example checklist would be appropriate as a debriefing after the procedure is complete.
1. Name of operative procedure(s): [procedure1] [procedure2]
2. Sponge, sharp, and instrument counts correct: Yes or N/A 3. Specimens identified and labeled: Yes or N/A
4. Specimens: [specimen1] [specimen2]
5. Equipment problems to be addressed; Yes or N/A
6. Wound Classification: [class]
7. Key concerns for recovery and management:
8. Debriefing with all team members regarding team performance, key events, changes to reference card: Done or N/A In each of these checklists, PM computer device 102 verifies that all of the information has been provided by the users 108. Once the information has been verified, PM computer device 102 summarizes the information for confirmation.

Below is an example process 100, where a surgeon (user 108) is in an operating room is scrubbed and ready to perform an operation.

First user 108 (surgeon) makes a statement 110, "OK let's get this Time-Out out of the way." In this embodiment, the term "Time-Out" activates PM computer device 102 to begin process 100. PM computer device 102 transmits through the speaker 106, "Time-Out Process About to Begin."

The user 108 (surgeon) makes an additional statement 110, "Today we are operating on Robert Jones. Medical record number: 00012345467. Date of birth is . . . What is it? (Nurse states Jun. 28, 1953). Thanks, Judy. We will be performing a total knee replacement. I am Doctor MacKenzie. My Assistant is Dr. Willie Sutton. We are using general, endotracheal anesthesia. OK, let's get started." PM computer device 102 receives the additional statement 110 through microphone 104. PM computer device 102 parses the additional statement 110 and determines that there is a discrepancy. A knee replacement could be done on either of two knees and the additional statement 110 did not include that information. PM computer device 102 generates a request for clarification 112. PM computer device 102 plays the request for clarification 112 through speaker 106, "The Knee Replacement Procedure has laterality. Which side has been marked for operation?" The user 108 (surgeon) replies with a clarification 114, "The left knee." PM computer device 102 acknowledges the clarification 114 and polls the other users in the room to confirm the clarification, "Left, got it. Is everyone in agreement?" (At this point, each member of the team identifies her (him)self and says "Yes" or "Agree") Once the confirmation is complete, PM computer device 102 continues, "OK, everyone is in agreement that we doing a left knee replacement on Robert Jones today. Please continue, Doctor."

PM computer device 102 then requests information on the next item on the checklist, "Is there blood available?" PM computer device 102 listens to the user comments in response to the latest question. User 108 (surgeon) "Hey, do we have blood?" Another user 108 (Circulating nurse): "Two units." Based on those statements, PM computer device 102 requests a clarification 112, "Two units of blood, is that correct?" User 108 (surgeon) replies with a clarification 114, "Yes, now let's go!"

PM computer device 102 then requests clarification 112 on the next item on the checklist, "Doctor, are the appropriate imaging studies available for viewing?" PM computer device 102 waits until user 108 replies with a clarification 114, "Oh, yeah, can you pull up the MRI?" Then PM computer device 102 continues to requests a clarification 112 on the next item on the checklist, "Has the antibiotic been given?" A user 108 (Anesthesiologist) states the clarification 114 "One gram of Ancef, IV push!"

PM computer device 102 then requests clarification 112 on the next item on the checklist, "Are the implants in the room?" PM computer device 102 receives a negative response from a user 108 (Circulating nurse) "I'll go get them right now!" PM computer device 102 waits until it receives a positive clarification 114 as this is a required item on the checklist. User 108 (Circulating nurse) (after a few minutes): "Implants are in the room!" PM computer device 102 then requests clarification 112 on the next item on the checklist, "Are there any allergies?" To which a user 108 (Circulating nurse) replies, "No allergies."

Once PM computer device 102 determines that the checklist is complete, PM computer device 102 generates a summation 116 and plays the summation 116 to the users 108, "The Time-Out Process is complete. Let's verify. Today, Doctor McKenzie and his assistant, Dr. Sutton, are performing a left knee replacement on Mr. Robert Jones. General, endotracheal anesthesia is being used. There are two units of blood available. The appropriate imaging studies are available. There are no allergies. Is this correct?" PM computer device 102 waits for confirmation 118 from a user 108, such as user 108 (surgeon) stating "Sure, now let's go!"

PM computer device 102 concludes process 100 and informs the users 108 by stating, "Information verified. Please alert me when the procedure is completed so that we activate the Debriefing Module. Have a nice day!" PM computer device 102 filters out non-useful statements made by the users 108, such as "Yeah, whatever. Why am I talking to a machine?"

Figure 2:
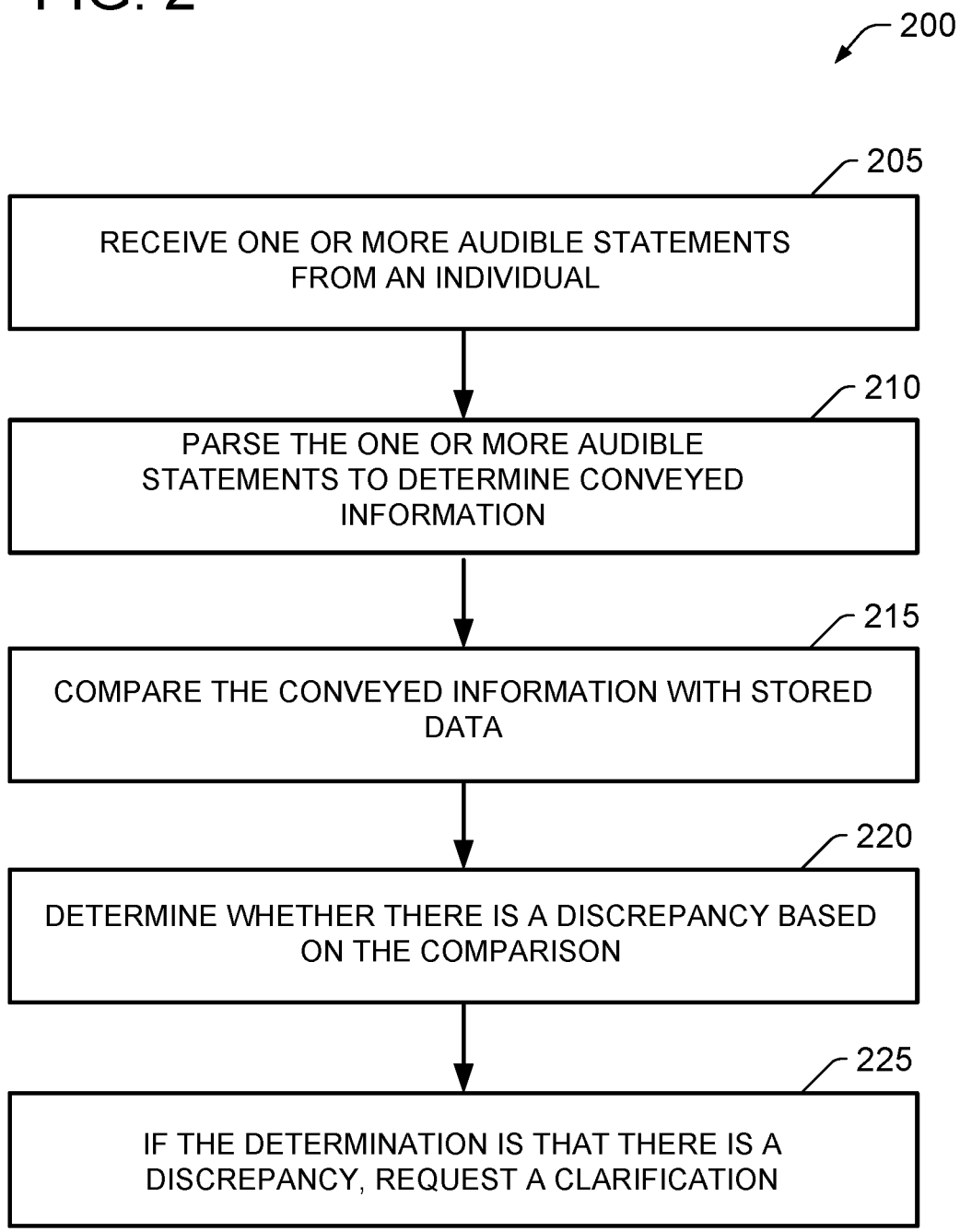
FIG. 2 illustrates a process flow chart of an exemplary computer-implemented process for voice-based procedure management as shown in FIG. 1.

FIG. 2 illustrates a process flow chart of an exemplary computer implemented process 200 for voice-based procedure management using process 100 shown in FIG. 1. Process 200 may be implemented by a computing device, for example procedure management computer device 102 (shown in FIG. 1) or PM server 310 (shown in FIG. 3).

In the exemplary embodiment, PM server 310 receives 205 one or more audible statements 110 (shown in FIG. 1) from an individual, such as user 108 (shown in FIG. 1) through a microphone 104 (shown in FIG. 1). The one or more audible statements are in a natural language form. PM server 310 parses 210 the one or more audible statements 110 to determine conveyed information. Conveyed information represents the information that user 108 desired to transmit to PM server 310. For example, the user 108 may state "I am Dr. Smith and am here to perform an appendectomy on Mr. Johnson, patient number #1234." PM server 310 then parses that statement 110 into the important details: Doctor—"Smith"; Patient—"Mr. Johnson"; Patient Number—"1234"; and operation—appendectomy. PM server 310 parses the statement into discrete data elements to allow normalized semantic definition of the meaning of conveyed information.

PM server 310 compares 215 the conveyed information with stored data. In the exemplary embodiment, PM server 310 stores a plurality of data about the procedure. This information includes data points about the procedure and/or the object of the procedure. In the above example, PM server 310 compares the important details parsed out of the statement with the stored data. PM server 310 determines 220 whether there is a discrepancy between the conveyed information and the stored data. If the data matches, then PM server 310 continues with the procedure. If there is a discrepancy, PM server 310 requests 225 a clarification 114 (shown in FIG. 1) through speaker 106 (shown in FIG. 1). In the exemplary embodiment, the request for clarification 112 (shown in FIG. 1) is a natural language question. PM server 310 then waits to receive a response from user. For example, user 108 may have misstated the patient number, which is actually 1235. In this example, PM server 310 may ask user 108 to repeat the patient number. Or PM server 310 may read back the patient number that user provided and point out the discrepancy and ask for clarification.

In the exemplary embodiment, PM server 310 stores both the conveyed information and the provided clarifications 114. In some embodiments, PM server 310 converts the data into a desired format prior to storing. In some further embodiments, the desired format is in fields in forms. In these embodiments, PM server 310 populates the fields in those forms based on the conveyed information and the provided clarifications 114.

In some embodiments, PM server 310 stores a checklist that includes one or more steps of the procedure. In these embodiments, each step of the checklist includes information that needs to be provided to complete that step. PM server 310 compares the conveyed information to the checklist and determines the discrepancy based on that comparison. For example, PM server 310 may determine that one or more steps of the procedure have not been performed. In these embodiments, PM server 310 transmits requests for clarification 112 to the user 108 that request information necessary to complete the next step.

When PM server 310 determines that all of the necessary information has been provided, PM server 310 generates a summation 116 (shown in FIG. 1) of the conveyed information and the provided clarifications 114. PM server 310 plays the summation 116 to the user 108 through the speaker 106. PM server 310 waits for the user 108 to confirm the summation 116 and stores both the summation 116 and the confirmation 118. Once confirmed, the structured data is then sent to the Database 320 to be added to the patient's electronic medical record.

Figure 3:
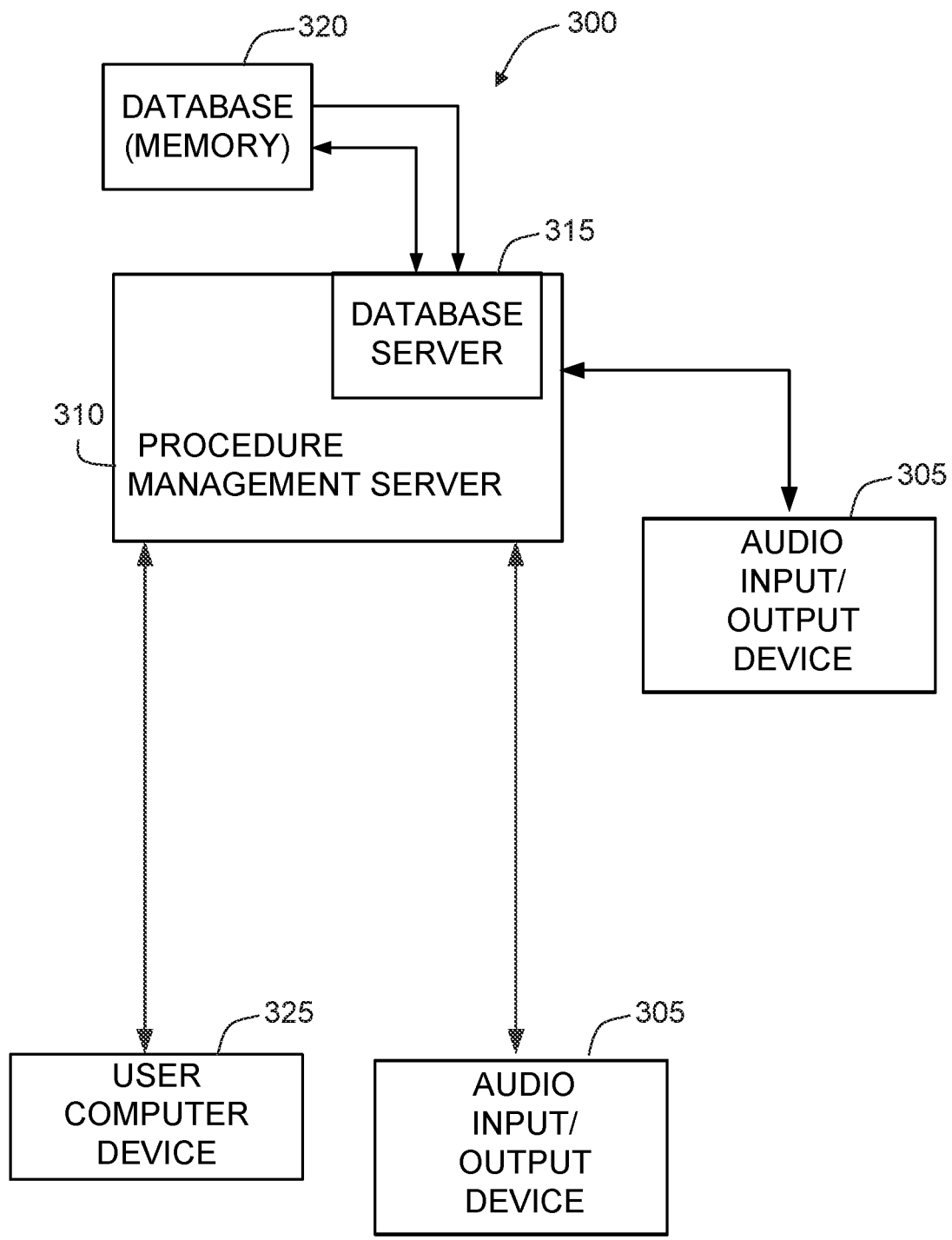
FIG. 3 illustrates a simplified block diagram of an exemplary computer system for implementing the data flow shown in FIG. 1 and the process flow shown in FIG. 2.

FIG. 3 depicts a simplified block diagram of an exemplary system 300 for implementing process 100 shown in FIG. 1 and/or process 200 shown in FIG. 2. In the exemplary embodiment, system 300 may be used for voice-based procedure management. As described below in more detail, a procedure management ("PM") server 310, which may be similar to procedure management computer device 102 (shown in FIG. 1), may be configured to (i) receive, via a microphone 104 (shown in FIG. 1), one or more audible statements from an individual, such as user 108 (shown in FIG. 1); (ii) parse the one or more audible statements 110 (shown in FIG. 1) to determine conveyed information; (iii) compare the conveyed information with stored data; (iv) determine whether there is a discrepancy based on the comparison; and if the determination is that there is a discrepancy, (v) request, via a speaker 106 (shown in FIG. 1), a clarification 114 (shown in FIG. 1).

In the exemplary embodiment, audio input/output devices 305 are capable of receiving and/or transmitting audio. In some embodiments, audio input/output devices 305 include both microphones 104 and speakers 106. In some further embodiments, audio input/output devices 305 may include multiple microphones 104 and speakers 106. In other embodiments, audio input/output devices 305 only include a microphone 104 or a speaker 106. In the exemplary embodiment, audio input/output devices 305 are capable of detecting and recording voice communication. In some embodiments, audio input/output devices 305 are configured to filter out background noise to improve reception of voice audio. Audio input/output devices 305 may be connected to PM server 310 through wired or wireless connections. More specifically, audio input/output devices 305 may be communicatively coupled to PM server 310 through many interfaces including, but not limited to, at least one of the Internet, a network, such as the Internet, a wireless local area network (WLAN), a local area network (LAN), a wide area network (WAN), or an integrated services digital network (ISDN), a dial-up-connection, a digital subscriber line (DSL), a cellular phone connection, a direct wired connection, such as a USB connection, and a cable modem.

In the exemplary embodiment, user computer devices 325 may be computers that include a web browser or a software application, which enables user computer devices 325 to access remote computer devices, such as PM server 310, using the Internet or other network. More specifically, user computer devices 325 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. User computer devices 325 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices.

A database server 315 may be communicatively coupled to a database 320 that stores transactional clinical and administrative data. In one embodiment, database 320 may include the procedures, data points, checklists, and forms. In the exemplary embodiment, database 320 may be stored remotely from PM server 310. In some embodiments, database 320 may be decentralized. In the exemplary embodiment, a user, such as user 102, may access database 320 via user computer device 325 by logging onto PM server 310, as described herein.

PM server 310 may be in communication with a plurality of audio input/output devices 305 and a plurality of user computer devices 325 to process procedure information. In some embodiments, PM server 310 may be located in a single room where a procedure is to take place and PM server 310 is in communication with audio input/output devices 305 in that room. In other embodiments, PM server 310 may be located in a remote location and in communication with a plurality of audio input/output devices 305 that are located in a plurality of locations where a plurality of procedures are taking place.

Figure 4:
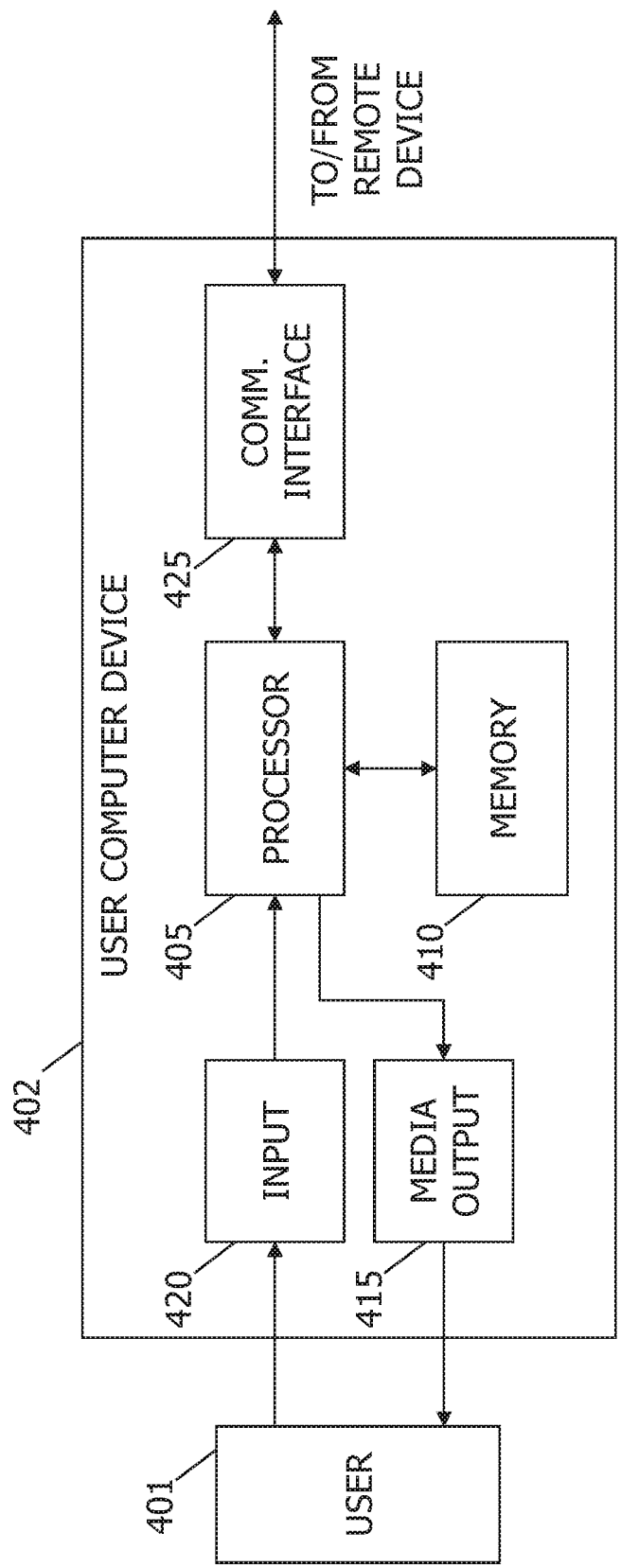
FIG. 4 illustrates an exemplary configuration of a client computer device, in accordance with one embodiment of the present disclosure.

FIG. 4 depicts an exemplary configuration of client computer device, in accordance with one embodiment of the present disclosure. User computer device 402 may be operated by a user 401. User computer device 402 may include, but is not limited to, audio input/output device 305 and user computer devices 325 (both shown in FIG. 3). User computer device 402 may include a processor 405 for executing instructions. In some embodiments, executable instructions may be stored in a memory area 410. Processor 405 may include one or more processing units (e.g., in a multi-core configuration). Memory area 410 may be any device allowing information such as executable instructions and/or transaction data to be stored and retrieved. Memory area 410 may include one or more computer readable media.

User computer device 402 may also include at least one media output component 415 for presenting information to user 401. Media output component 415 may be any component capable of conveying information to user 401. In some embodiments, media output component 415 may include an output adapter (not shown) such as a video adapter and/or an audio adapter. An output adapter may be operatively coupled to processor 405 and operatively coupleable to an output device such as a display device (e.g., a cathode ray tube (CRT), liquid crystal display (LCD), light emitting diode (LED) display, or "electronic ink" display) or an audio output device (e.g., a speaker or headphones).

In some embodiments, media output component 415 may be configured to present a graphical user interface (e.g., a web browser and/or a client application) to user 401. A graphical user interface may include, for example, a checklist or a completed form. In some embodiments, user computer device 402 may include an input device 420 for receiving input from user 401. User 401 may use input device 420 to, without limitation, convey audio information, such as shown in FIG. 1.

Input device 420 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 415 and input device 420.

User computer device 402 may also include a communication interface 425, communicatively coupled to a remote device such as PM server 310 (shown in FIG. 3). Communication interface 425 may include, for example, a wired or wireless network adapter and/or a wireless data transceiver for use with a mobile telecommunications network.

Stored in memory area 410 are, for example, computer readable instructions for providing a user interface to user 401 via media output component 415 and, optionally, receiving and processing input from input device 420. A user interface may include, among other possibilities, a web browser and/or a client application. Web browsers enable users, such as user 401, to display and interact with media and other information typically embedded on a web page or a website from PM server 310. A client application may allow user 401 to interact with, for example, PM server 310. For example, instructions may be stored by a cloud service, and the output of the execution of the instructions sent to the media output component 415.

Figure 5:
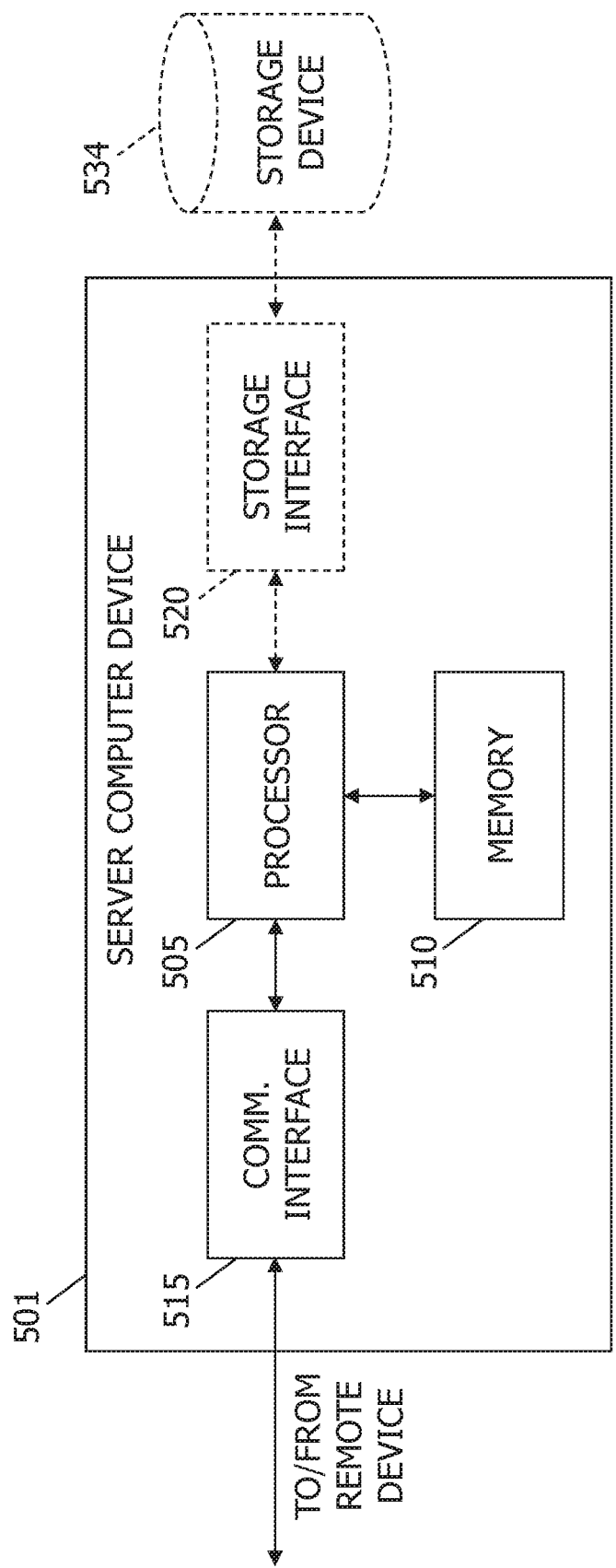
FIG. 5 illustrates an exemplary configuration of the PM computer device, in accordance with one embodiment of the present disclosure.

FIG. 5 depicts an exemplary configuration of PM computer device 102, in accordance with one embodiment of the present disclosure. Server computer device 501 may include, but is not limited to, PM computer device 102 (shown in FIG. 1), PM server 310, and database server 315 (all shown in FIG. 3). Server computer device 501 may also include a processor 505 for executing instructions. Instructions may be stored in a memory area 510. Processor 505 may include one or more processing units (e.g., in a multi-core configuration).

Processor 505 may be operatively coupled to a communication interface 515 such that server computer device 501 is capable of communicating with a remote device such as another server computer device 501, PM server 310, audio input/output device 305, user computer device 325 (all shown in FIG. 3) (for example, using wireless communication or data transmission over one or more radio links or digital communication channels). For example, communication interface 515 may receive requests from user computer devices 325 via the Internet, as illustrated in FIG. 3.

Processor 505 may also be operatively coupled to a storage device 534. Storage device 534 may be any computer-operated hardware suitable for storing and/or retrieving data, such as, but not limited to, data associated with database 320 (shown in FIG. 3). In some embodiments, storage device 534 may be integrated in server computer device 501. For example, server computer device 501 may include one or more hard disk drives as storage device 534.

In other embodiments, storage device 534 may be external to server computer device 501 and may be accessed by a plurality of server computer devices 501. For example, storage device 534 may include a storage area network (SAN), a network attached storage (NAS) system, and/or multiple storage units such as hard disks and/or solid state disks in a redundant array of inexpensive disks (RAID) configuration.

In some embodiments, processor 505 may be operatively coupled to storage device 534 via a storage interface 520. Storage interface 520 may be any component capable of providing processor 505 with access to storage device 534. Storage interface 520 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 505 with access to storage device 534.

Processor 505 may execute computer-executable instructions for implementing aspects of the disclosure. In some embodiments, the processor 505 may be transformed into a special purpose microprocessor by executing computer-executable instructions or by otherwise being programmed. For example, the processor 505 may be programmed with the instruction such as illustrated in FIG. 2.

Figure 6:
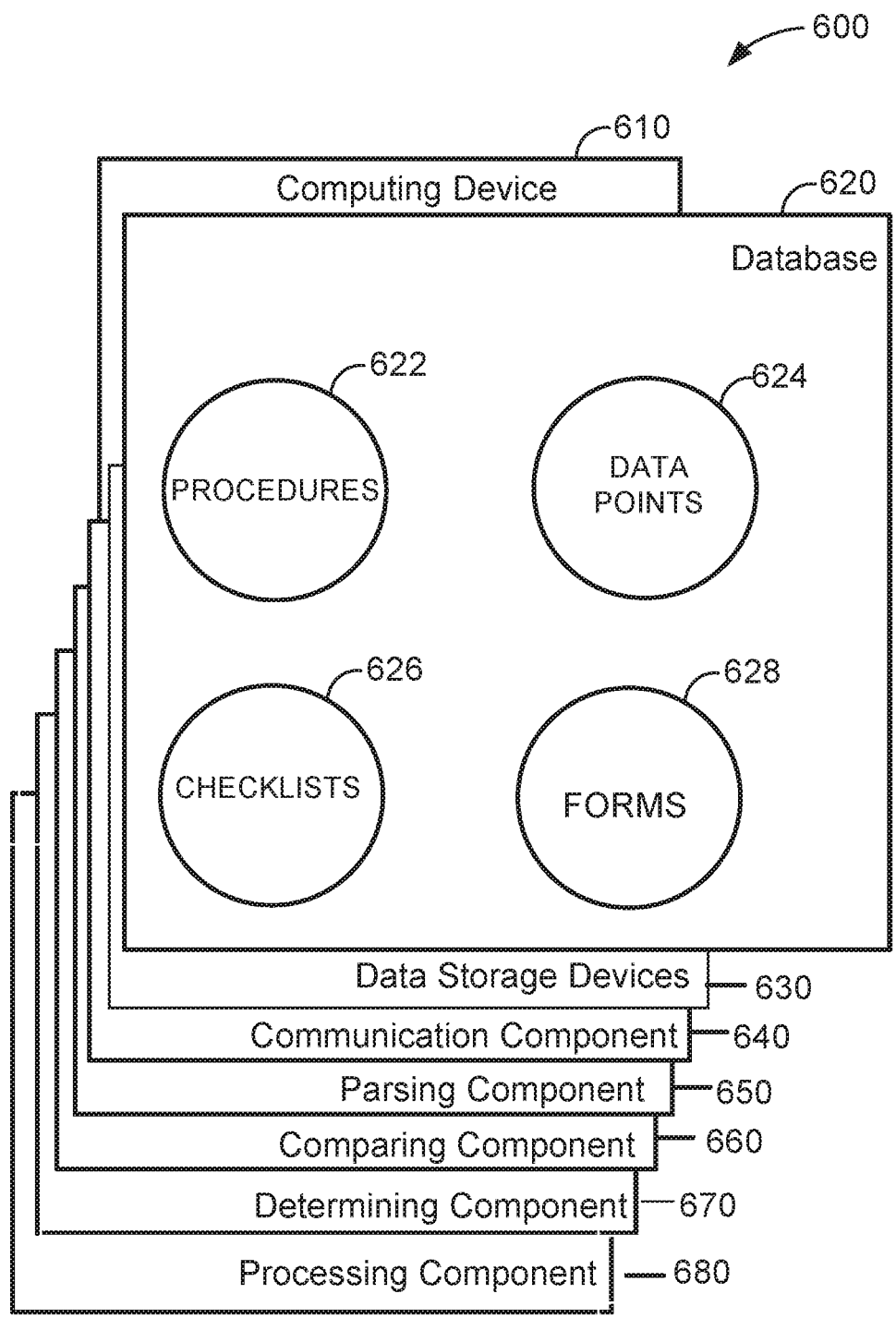
FIG. 6 illustrates a diagram of components of one or more exemplary computing devices that may be used in the system shown in FIG. 3.

FIG. 6 depicts a diagram 600 of components of one or more exemplary computing devices 610 that may be used to implement process 100 shown in FIG. 1 and system 300 shown in FIG. 3. In some embodiments, computing device 610 may be similar to PM computer device 102 (shown in FIG. 1) and/or PM server 310 (shown in FIG. 3). Database 620 may be coupled with several separate components within computing device 610, which perform specific tasks. In this embodiment, database 620 may include the procedures 622, data points 624, checklists 626, and forms 628. In some embodiments, database 620 is similar to database 320 (shown in FIG. 3).

Computing device 610 may include the database 620, as well as data storage devices 630. Computing device 610 may also include a communication component 640 for receiving 205 one or more audible statements from a user and requesting 225 a clarification (both shown in FIG. 2). Computing device 610 may further include a parsing component 650 for parsing 210 the one or more audible statements. Moreover, computing device 610 may include a comparing component 660 for comparing 215 the conveyed information (shown in FIG. 2). In addition, computing device 610 may include a determining component 670 for determining 220 whether there is a discrepancy (shown in FIG. 2). A processing component 680 may assist with execution of computer-executable instructions associated with the system.

The computer-implemented methods discussed herein may include additional, less, or alternate actions, including those discussed elsewhere herein. The methods may be implemented via one or more local or remote processors, transceivers, servers, and/or sensors (such as processors, transceivers, servers, and/or sensors mounted in rooms where specific procedures take place or mobile devices), and/or via computer-executable instructions stored on non-transitory computer-readable media or medium.

In some embodiments, the design system is configured to implement machine learning, such that the neural network "learns" to analyze, organize, and/or process data without being explicitly programmed. Machine learning may be implemented through machine learning (ML) methods and algorithms. In an exemplary embodiment, a machine learning (ML) module is configured to implement ML methods and algorithms. In some embodiments, ML methods and algorithms are applied to data inputs and generate machine learning (ML) outputs. Data inputs may include but are not limited to: analog and digital signals (e.g. sound, light, motion, natural phenomena, etc.) Data inputs may further include: sensor data, image data, video data, and telematics data. ML outputs may include but are not limited to: digital signals (e.g. information data converted from natural phenomena). ML outputs may further include: speech recognition, image or video recognition, medical diagnoses, statistical or financial models, autonomous vehicle decision-making models, robotics behavior modeling, fraud detection analysis, user input recommendations and personalization, game AI, skill acquisition, targeted marketing, big data visualization, weather forecasting, and/or information extracted about a computer device, a user, a home, a vehicle, or a party of a transaction. In some embodiments, data inputs may include certain ML outputs.

In some embodiments, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various embodiments, the implemented ML methods and algorithms are directed toward at least one of a plurality of categorizations of machine learning, such as supervised learning, unsupervised learning, and reinforcement learning.

In one embodiment, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above. For example, a ML module may receive training data comprising customer identification and geographic information and an associated customer category, generate a model which maps customer categories to customer identification and geographic information, and generate a ML output comprising a customer category for subsequently received data inputs including customer identification and geographic information.

In another embodiment, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In an exemplary embodiment, a ML module coupled to or in communication with the design system or integrated as a component of the design system receives unlabeled data comprising customer purchase information, customer mobile device information, and customer geolocation information, and the ML module employs an unsupervised learning method such as "clustering" to identify patterns and organize the unlabeled data into meaningful groups. The newly organized data may be used, for example, to extract further information about the circuit.

In yet another embodiment, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In an exemplary embodiment, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict optimal constraints.

In some embodiments, the ML module may learn how to verify that the users performing the procedure have the necessary information to properly perform the procedure in question. Accordingly, the ML module instructs the PM computer device 102 (shown in FIG. 1) to phrase statements to simply ask for or confirm the details necessary. The ML module may also instruct the PM computer device 102 to filter out unnecessary comments. Furthermore, the ML module may recognize patterns and be able to apply those patterns when generating clarifying statements and/or understanding user statements to improve the efficiency of that process and reduce processing resources.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some embodiments, the system includes multiple components distributed among a plurality of computer devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment," "exemplary embodiment," or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for operating a voice-based artificial intelligence controller comprising:
   a microphone;
   a speaker; and
   a computer device in communication with said microphone and said speaker, said computer device including at least one processor in communication with at least one memory device, said computer device programmed to:
   receive, via said microphone, one or more audible statements from a first individual;
   receive, via said microphone, one or more additional audible statements from a second individual;
   parse the one or more audible statements and the one or more additional audible statements to determine conveyed information;
   compare the conveyed information with stored data;
   determine whether there is a discrepancy based on the comparison;
   determine which individual is associated with the discrepancy; and
   if the determination is that there is a discrepancy, request, via said speaker, a clarification from the individual associated with the discrepancy; and receive, via said microphone, the clarification from the individual associated with the discrepancy.

2. A system in accordance with claim 1, wherein said computer device is further programmed to:
   transmit, via said speaker, a statement; and
   request, via said speaker, confirmation from each of the plurality of individuals.

3. A system in accordance with claim 1, wherein said computer device is further programmed to:
   combine the conveyed information and the clarification into a desired format; and
   store, in the at least one memory device, the conveyed information and the clarification in the desired format.

4. A system in accordance with claim 1, wherein said computer device is further programmed to fill out a form based on the conveyed information.

5. A system in accordance with claim 1, wherein said computer device is further programmed to:
   store a checklist including one or more steps of a procedure;
   compare the conveyed information to the checklist; and
   determine the discrepancy based on the comparison.

6. A system in accordance with claim 5, wherein said computer device is further programmed to:
   determine a next step of the one or more steps of the procedure; and
   generate the clarification based on the next step.

7. A system in accordance with claim 1, wherein said computer device is further programmed to:
   generate a summary based on the conveyed information;
   transmit, via said speaker, the summary to at least one of the first individual and the second individual for confirmation; and
   receive, via said microphone, confirmation from the corresponding individual.

8. A system in accordance with claim 1, wherein said computer device is further programmed to:
   receive a plurality of statements from a plurality of individuals; and
   parse the plurality of statements to determine the conveyed information.

9. A system in accordance with claim 8, wherein each individual of the plurality of individuals is associated with a role, and wherein said computer device is further programmed to:
   identify each individual of the plurality of individuals;
   determine a role associated with each individual of the plurality of individuals; and
   associate the conveyed information associated with that individual with the role associated with the individual.

10. A system in accordance with claim 1, wherein said computer device is further programmed to:
    store one or more data points;
    compare the conveyed information to the one or more data points; and
    determine the discrepancy based on the comparison.

11. A system in accordance with claim 1, wherein the one or more audible statements are in a natural language form.

12. A system in accordance with claim 1, wherein the clarification is a question in a natural language form.

13. A computer system for operating a voice-based artificial intelligence controller, the computer system including at least one processor in communication with at least one memory device, the at least one processor is programmed to:
    receive, via a microphone, one or more audible statements from a first individual;
    receive, via the microphone, one or more additional audible statements from a second individual;
    parse the one or more audible statements and the one or more additional audible statements to determine conveyed information;
    compare the conveyed information with stored data;
    determine whether there is a discrepancy based on the comparison;
    determine which individual is associated with the discrepancy; and
    if the determination is that there is a discrepancy, request, via a speaker, a clarification from the individual associated with the discrepancy; and receive, via said microphone, the clarification from the individual associated with the discrepancy.

14. The computer system of claim 13, wherein the processor is further programmed to fill out a form based on the conveyed information.

15. The computer system of claim 13, wherein the processor is further programmed to:
    store a checklist including one or more steps of a procedure;
    compare the conveyed information to the checklist; and
    determine the discrepancy based on the comparison.

16. The computer system of claim 15, wherein the processor is further programmed to:
    determine a next step of the one or more steps of the procedure; and
    generate the clarification based on the next step.

17. The computer system of claim 13, wherein the processor is further programmed to:
    generate a summary based on the conveyed information;
    transmit, via the speaker, the summary to the individual for confirmation; and
    receive, via the microphone, confirmation from the individual.

18. The computer system of claim 13, wherein the processor is further programmed to:
    receive a plurality of statements from a plurality of individuals, wherein each individual of the plurality of individuals is associated with a role;
    parse the plurality of statements to determine the conveyed information;
    identify each individual of the plurality of individuals;
    determine a role associated with each individual of the plurality of individuals; and
    associate the conveyed information associated with that individual with the role associated with the individual.

19. The computer system of claim 13, wherein the processor is further programmed to:
    store one or more data points;
    compare the conveyed information to the one or more data points; and
    determine the discrepancy based on the comparison.

20. A computer-based method for operating a voice-based artificial intelligence controller, the method is implemented on a computer device including at least one processor in communication with at least one memory device, the method comprising:
    receiving, via a microphone, one or more audible statements from a first individual;
    receiving, via the microphone, one or more additional audible statements from a second individual;
    parsing the one or more audible statements and the one or more additional audible statements to determine conveyed information;
    comparing the conveyed information with stored data;
    determining whether there is a discrepancy based on the comparison;
    determining which individual is associated with the discrepancy; and
    if the determination is that there is a discrepancy, requesting, via a speaker, a clarification from the individual associated with the discrepancy; and receiving, via the microphone, the clarification from the individual associated with the discrepancy.

* * * * *